United States Patent
Serbousek et al.

(10) Patent No.: US 6,949,124 B2
(45) Date of Patent: *Sep. 27, 2005

(54) PROSTHESIS WITH FEATURE ALIGNED TO TRABECULAE

(75) Inventors: Jon C. Serbousek, Memphis, TN (US); Thomas S. Camino, Warsaw, IN (US); J. Brock Vanmeter, Leesburg, IN (US); Marc G. Weissman, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/670,092

(22) Filed: Sep. 24, 2003

(65) Prior Publication Data

US 2004/0059427 A1 Mar. 25, 2004

Related U.S. Application Data

(63) Continuation of application No. 09/989,123, filed on Nov. 20, 2001, now Pat. No. 6,652,591.
(60) Provisional application No. 60/255,644, filed on Dec. 14, 2000.

(51) Int. Cl.[7] .................................................. A61F 2/36
(52) U.S. Cl. ................................ 623/23.31; 623/23.15
(58) Field of Search .......................... 623/23.31, 23.15, 623/19.14, 22.11, 23.13

(56) References Cited

U.S. PATENT DOCUMENTS

| | | |
|---|---|---|
| 3,855,638 A | 12/1974 | Pilliar |
| 3,894,297 A | 7/1975 | Mittelmeier et al. |
| 4,031,571 A | 6/1977 | Heimke et al. |
| 4,163,292 A | 8/1979 | Averett, Jr. |
| 4,199,824 A | 4/1980 | Niederer |
| 4,206,516 A | 6/1980 | Pilliar |
| 4,306,550 A | 12/1981 | Forte |
| 4,430,761 A | 2/1984 | Niederer et al. |
| 4,546,501 A | 10/1985 | Gustilo et al. |
| 4,589,883 A | 5/1986 | Kenna |
| 4,623,349 A | 11/1986 | Lord |
| 4,661,112 A | 4/1987 | Muller |
| 4,664,668 A | 5/1987 | Beck et al. |

(Continued)

FOREIGN PATENT DOCUMENTS

| | | |
|---|---|---|
| EP | 0 169 976 B1 | 2/1986 |
| EP | 0 965 312 B1 | 12/1999 |

OTHER PUBLICATIONS

BIOMET® Inc., Bio–Groove® HA Enhanced, 16 pages, Form No. Y–BMT–264/123192, Biomet, Inc. Warsaw, Indiana 46580 ©1 992 Biomet, Inc., Biomet Ltd., Waterton Industrial Estate, Bridgend, South Glamorgan CF31 3YN, UK.

(Continued)

*Primary Examiner*—Cary E. O'Connor
*Assistant Examiner*—Candice C. Stokes

(57) ABSTRACT

A ball and socket joint prosthesis for use in arthroplasty is provided. The prosthesis includes a body for implantation at least partially within the medullary canal of a long bone. The long bone defines trabeculae in the proximal cancellous bone and lamellae in the cortical bone. The body includes a proximal portion thereof and a distal portion. The proximal portion has a medial periphery and includes surface features on a substantial portion of its proximal portion. The surface features are positioned to optimally transfer load from the prosthesis to the long bone.

5 Claims, 13 Drawing Sheets

U.S. PATENT DOCUMENTS

| | | |
|---|---|---|
| 4,673,409 A | 6/1987 | Van Kampen |
| 4,704,128 A | 11/1987 | Frey |
| 4,714,470 A | 12/1987 | Webb, Jr. et al. |
| 4,790,852 A | 12/1988 | Noiles |
| 4,795,472 A | 1/1989 | Crowninshield et al. |
| 4,840,632 A | 6/1989 | Kampner |
| 4,840,633 A | 6/1989 | Kallabis et al. |
| 4,865,608 A | 9/1989 | Brooker, Jr. |
| 5,004,475 A | 4/1991 | Vermeire |
| 5,013,324 A | 5/1991 | Zolman et al. |
| 5,062,854 A | 11/1991 | Noble et al. |
| 5,147,408 A | 9/1992 | Noble et al. |
| 5,152,799 A | 10/1992 | Lyons |
| 5,163,963 A | 11/1992 | Hewka et al. |
| 5,171,275 A | 12/1992 | Ling et al. |
| 5,192,323 A | 3/1993 | Shetty et al. |
| 5,194,066 A | 3/1993 | Van Zile |
| 5,290,318 A | 3/1994 | Ling et al. |
| 5,314,479 A | 5/1994 | Rockwood, Jr. et al. |
| 5,314,489 A | 5/1994 | Hoffman et al. |
| 5,342,362 A | 8/1994 | Kenyon et al. |
| 5,368,881 A | 11/1994 | Kelman et al. |
| 5,458,653 A | 10/1995 | Davidson |
| 5,496,375 A | 3/1996 | Sisk et al. |
| 5,507,829 A | 4/1996 | Thongpreda et al. |
| 5,549,690 A | 8/1996 | Hollister et al. |
| 5,658,333 A | 8/1997 | Kehman et al. |
| 5,728,161 A | 3/1998 | Camino et al. |
| 5,733,338 A | 3/1998 | Kampner |
| 5,776,204 A | 7/1998 | Noble et al. |
| 5,935,172 A | 8/1999 | Ochoa et al. |
| 6,007,581 A | 12/1999 | Noble et al. |
| 6,008,432 A | 12/1999 | Taylor |
| 6,013,104 A | 1/2000 | Kampnerq |
| 6,017,366 A | 1/2000 | Berman |
| 6,033,439 A | 3/2000 | Camino et al. |
| 6,120,542 A | 9/2000 | Camino et al. |
| 6,436,148 B1 * | 8/2002 | DeCarlo et al. ......... 623/23.15 |
| 6,652,591 B2 * | 11/2003 | Serbousek et al. ....... 623/23.31 |

OTHER PUBLICATIONS

LINK®, Link® C.F.P. Hip Stems—Link® T.O.P Acetabular Cups—Can "Bioharmony" be Achieved?, 1 page, Waldemar Link GmbH & Co—Barkhausenweg 10—D 22339 Hamburg—P.O. Box 63 05 52—D–22315 Hamburg.

STRYKER® Howmedica Osteonics, Knees—Confidence, Succession, 2 pages, 359 Veterens Blvd, Rutherford, NJ 07070—59 Route 17 South, Allendale, NJ 07401.

Osteonics Corp., Omni–Fit®—Extended Indications System; 16 pages; 59 Route 17, Allendale, NJ 074001.

Biomet, Inc., The Ostopcap RS™, 14 pages, Form No. Y–BMT–511/022897/M, P.O. Box 587, Warsaw, IN 48581–0587, ©1997 Biomet, Inc.

Wright Medical Techology®, Perfecta® RS Femoral Stems Surgical Technique, 12 pages, © 1998, Wright Medical Technology, Inc., 5677 Airline Raod, Arlington, TN 38002.

Osteonics, Secur–Fit™ Plus Hydroxylapatite Coated System, 6 pages, Printed in USA, © Osteonics Corp. 1995, Spec. Dec. 1995, 59 Route 17, Allendale, NJ 07401.

Joint Implant Surgery and Research Foundation—Timothy McTihge, Director Stability™ Cementless Stem, 50 pages, 8183 Stoney Brook Drive, Chagrin Falls, OH 44022; P.O. Box, 16004, Jackson, MI 39236–6004.

DePuy, Inc., Uni–Rom® Total Hip system Surgical Technique, 8 pages, Printed in USA © 1999 DePuy Orthopaedics, Inc. 700 Orthopaedic Drive, Warsaw, IN 48580 USA; DePuy International Ltd., St Anthony's Road, Leeds LS11 8DT, England.

* cited by examiner

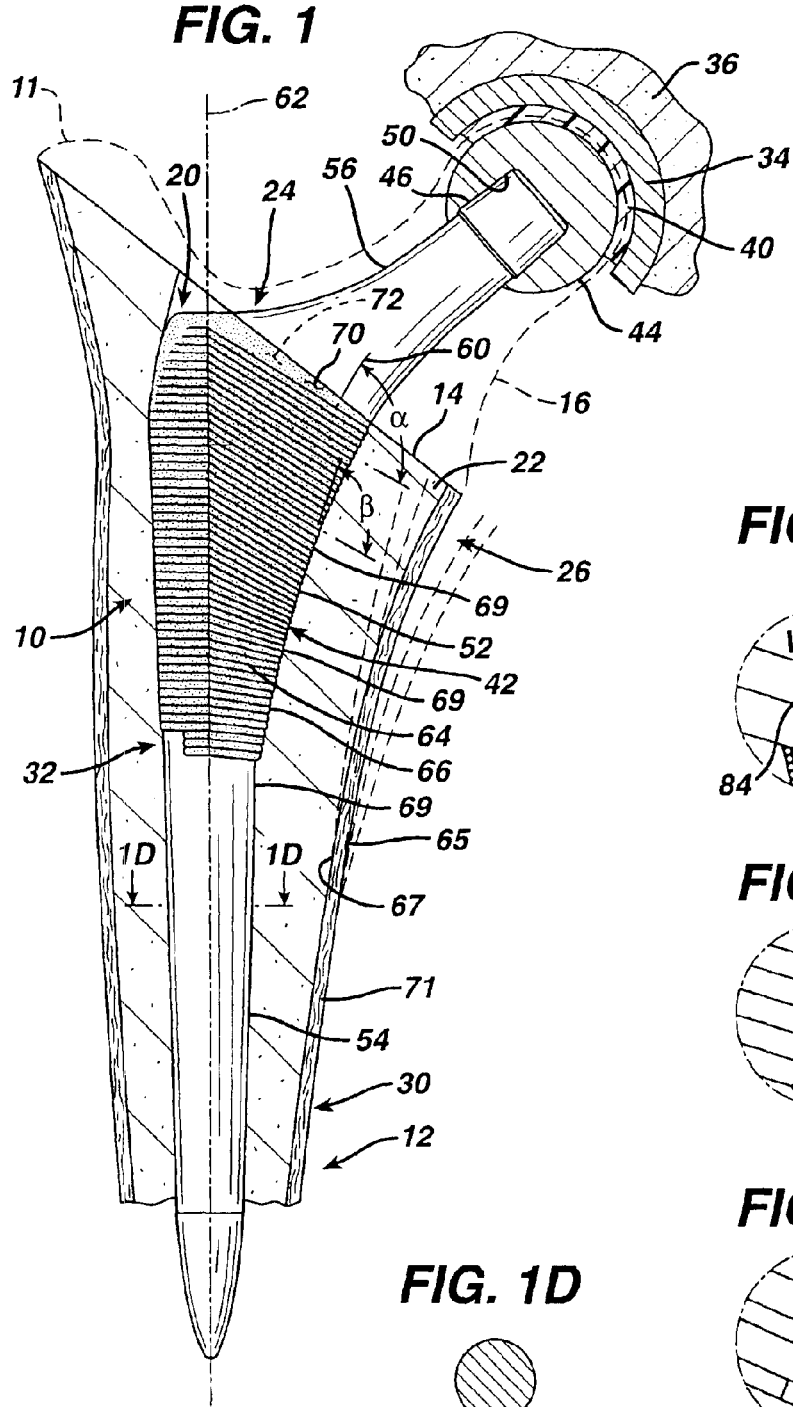
FIG. 1
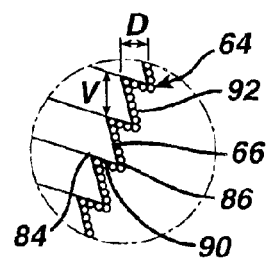
FIG. 1A
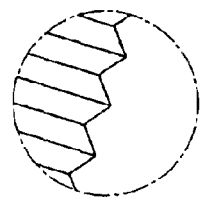
FIG. 1B
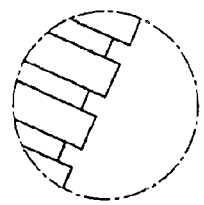
FIG. 1C
FIG. 1D

PROSTHESIS WITH FEATURE ALIGNED TO TRABECULAE

CROSS REFERENCE TO RELATED APPLICATIONS

This Application is a continuation of application Ser. No. 09/989,123 filed Nov. 20, 2001, now U.S. Pat. No. 6,652,591 based upon U.S. Provisional Patent Application, Ser. No. 60/255,644 filed Dec. 14, 2000, entitled PROSTHESIS WITH FEATURE ALIGNED TO TRABECULAE. The disclosures of U.S. Provisional Application Ser. No. 60/255,644 and U.S. application Ser. No. 09/989,123 are hereby totally incorporated by reference in their entireties.

TECHNICAL FIELD OF THE INVENTION

The present invention relates generally to the field of orthopaedics, and more particularly, to an implant for use in arthroplasty.

BACKGROUND OF THE INVENTION

The invention relates to implantable articles and methods for manufacturing such articles. More particularly, the invention relates to bone prosthesis and processes for manufacturing the same.

There are known to exist many designs for and methods for manufacturing implantable articles, such as bone prosthesis. Such bone prosthesis include components of artificial joints, such as elbows, hips, knees, and shoulders. An important consideration in the design and manufacture of virtually any implantable bone prosthesis is that the prosthesis has adequate fixation when implanted within the body.

Early designs of implantable articles relied upon the use of cements such as polymethylmethacrylate to anchor the implant. The use of such cements can have some advantages, such as providing a fixation that does not develop freeplay or does not lead to erosion of the joining bone faces postoperatively. However, the current trend is to use these cements to a lesser extent because of their tendency to lose adhesive properties over time and the possibility that the cement contributes to wear debris within a joint.

Recently, implantable bone prosthesis have been designed such that they encourage the growth of hard tissue (i.e., bone) around the implant. The bone attachment usually occurs and growth is promoted when the surface of the implantable bone prosthesis is irregular or textured. The interaction of newly formed hard tissue in and around the textured surface of the implantable bone prosthesis has been found to provide a good fixation of the prosthesis within the body. A greater degree of bone fixation can usually be achieved where bone-engaging surfaces of an implantable bone prosthesis are more porous or irregular.

Porous or irregular surfaces can be provided in implantable articles by a variety of techniques. In some instance, an irregular surface pattern or surface porosity is formed in an implantable bone prosthesis by embossing, chemical etching, milling or machining.

Another problem which has been observed in the use of known hip joint systems relates to the proper distribution of stresses within the prosthesis and throughout the surrounding bone. If too little stress is applied to the bone, resorption can occur leading to atrophy of the affected area. Too much stress may also lead to resorption and atrophy, or may result in an undesirable hypertrophy of the affected area. In some prior art, femoral stem designs excessive forces are transmitted through the relatively rigid stem to the distal portion, resulting in hypertrophy of the bone surrounding the distal portion, and atrophy of the bone surrounding the proximal portion of the stem. Accordingly, there exists a need for an improved hip joint prosthesis which addresses these needs and other problems of prior hip joint designs.

Attempts have been made to provide for proximal loading of the prosthesis within the bone. For example, in U.S. Pat. No. 5,004,075 to Vermeire a series of parallel spaced apart linear grooves 28 were positioned perpendicular to the longitudinal axis 22 of the neck of the prosthesis. A second set of parallel spaced apart linear grooves 29 were positioned generally perpendicular to the grooves 28. These grooves serve to provide support in the proximal region of the stem of this prosthesis.

In U.S. Pat. No. 4,865,608 to Brooker, Jr. a series of spaced apart parallel grooves 24 and 24' were positioned along the outer periphery of the opposite sides of the proximal portion of the stem. The grooves were positioned at an angle of approximately 70 degrees with respect to the longitudinal axis of the stem.

In total hip arthroplasty, initial and long term success are achieved through the use of a device which is designed to provide at least two features. The first of these features is the stable initial or immediate postoperative fixation within the femur. The second feature is the means to provide an optimal environment for a long-term stability in the femur. In the past, fixation has been achieved through the use of bone cement, porous coatings and bio-ceramics. Bio-ceramics includes such compositions as hydroxyapatite and tricalcium phosphates. Many of these cements, coatings and bio-ceramics have provided good clinical outcomes, however, none have addressed the biomechanics of load transmission through the proximal femur.

Methods of achieving femoral fixation in the prior art have met with some success. These methods include simple press fit, surface roughness, porous coating, and bioceramics. Many devices have included texturing to transfer load in favorable mechanical modes. However, none of the prior art devices have designed the texturing (steps) to transfer load along the natural load paths of the proximal femur. The Brooker patent has angled steps on the anterior and posterior face, however, on the medial edge, the steps are longitudinal. This design will not appropriately transmit load to the medial calcar. The Vermeire patent has no steps on the medial edge, posing a similar problem.

A commercially available product from Stryker Howmedica Osteonics known as the Omni Fit Femoral Stem has normalization features which transmit load directly vertical. This load path is not natural. This device has no medial steps. A commercially available product from DePuy Orthopaedics, Inc., the JMP S-ROM transmits axial loads, but again, does not follow the natural load path.

SUMMARY OF THE INVENTION

Accordingly, a need has arisen for a prosthesis which achieves fixation to the long bone by designing features to transfer load along the natural load paths of the proximal long bone.

The present invention includes a proximal long bone prosthesis which has been designed to provide initial stability and long term fixation through a series of features capable of transmitting load to the proximal long bone in a manner consistent with the natural load paths of the long bone. The long bone may be a femur, a humerus or any other long bone.

The present invention allows reconstruction of the proximal long bone with a device that is specifically designed to provide stable initial fixation and long term stability by optimally transferring load along the natural load lines through the femur. The load paths through the proximal long bone are seen by both the alignment of the trabeculae in the proximal cancellous bone and by the direction of the layers or lamellae in the cortical bone.

This device achieves initial fixation through a press fit. The press fit is achieved with a properly designed preparation instrumentation. Long term stability is achieved through a series of steps which are aligned normal to the trabeculae of the proximal femur cancellous bone and the lamellae of the proximal femoral cortex. The steps transmit load normal to their surface and hence along the natural femoral load lines. This replication of the natural femoral load paths lead to favorable remodeling of the proximal long bone. This fixation mode may be further enhanced with a bone in growth/on growth surface such as for example surface roughness, porous coating and/or bioceramics.

According to one embodiment of the present invention, a ball and socket joint prosthesis for use in arthroplasty is provided. The prosthesis includes a body for implantation at least partially within the medullary canal of a long bone. The long bone defines trabeculae in the proximal cancellous bone and lamellae in the cortical bone. The body includes a proximal portion and a distal portion. The proximal portion has a medial periphery and includes surface features on a substantial portion of the periphery of the proximal portion. The surface features are positioned to optimally transfer load from the prosthesis to the long bone.

According to another embodiment of the present invention, a hip-joint prosthesis for use in arthroplasty is provided. The prosthesis includes a body for implantation at least partially within the medullary canal of a long bone. The long bone has trabeculae in the proximal cancellous bone and has lamellae in the cortical bone. The body includes a proximal portion and a distal portion. The proximal portion has a medial periphery and includes a plurality of ribs extending from a substantial portion of the periphery of the proximal portion. The ribs are positioned so that the first direction of the ribs is from about 70 degrees to about 110 degrees with respect to the trabeculae in the proximal cancellous bone, the normal lamellae in the cortical bone or the medial periphery of the proximal portion of said body.

According to yet another embodiment of the present invention, a joint prosthesis for use in arthroplasty is provided. The prosthesis includes a body for implantation at least partially within the medullary canal of a long bone. The long bone includes trabeculae in the proximal cancellous bone and lamellae in the cortical bone. The body includes a proximal portion and a distal portion. The proximal portion has a medial periphery and includes surface features on a substantial portion of the periphery of the proximal portion. The surface features are positioned to optimally transfer load from the prosthesis to the long bone.

According to a further embodiment of the present invention, a stem for use in a joint prosthesis for implantation at least partially within the medullary canal of a long bone is provided. The long bone includes trabeculae in the proximal cancellous bone and lamellae in the cortical bone. The stem includes a proximal portion and a distal portion. The proximal portion has a medial periphery and surface features on a substantial portion of the periphery of the proximal portion. The surface features are positioned to optimally transfer load from the prosthesis to the long bone.

According to another embodiment a method for producing a joint prosthesis for use in arthroplasty is provided. The method includes the steps of providing a body including a proximal portion and a distal portion, the proximal portion having a medial periphery thereof, placing surface features on a substantial portion of the periphery of the proximal portion of the body, positioning the surface features to optimally transfer load from the prosthesis to the long bone, and implanting the prosthesis at least partially within the medullary canal of a long bone.

The technical advantages of the present invention include the ability to transmit loads to the proximal femur along the natural load lines. The load lines or load paths through the proximal femur are seen by both the alignment of the trabeculae in the proximal cancellous bone and by the direction of the lamellae in the cortical bone. This invention achieves initial fixation through a press-fit achieved with properly design preparation instrumentation. Long term stability is achieved through a series of steps which are aligned normal to the trabeculae of the proximal femoral cancellous bone and the lamellae of the proximal femoral cortex. The steps transmit load normal to their surface and hence along natural femoral load lines.

Another technical advantage of the present invention includes the ability to provide long term stability and fixation by providing an environmental optimum for femoral bone remodeling. The long term stability achieved through the series of steps which are aligned normal to the trabeculae of the proximal femoral cancellous bone and the lamellae of the proximal femoral cortex transmit load normal to their surface and hence along the natural femoral load lines. This replication of the natural femoral load paths leads to favorable remodeling of the proximal femoral bone. This fixation mode may be further enhanced with a bone ingrowth or ongrowth surface, for example, by providing for surface roughness, porous coating and bioceramics.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 1 is a plan view of a hip prosthesis in accordance with an embodiment of the present invention;

FIG. 1A is a partial enlarged view of the hip prosthesis of FIG. 1 showing steps on the periphery of the prosthesis in greater detail;

FIG. 1B is a partial enlarged view of the hip prosthesis of FIG. 1 showing steps with an alternate construction to those of FIG. 1A on the periphery of the prosthesis;

FIG. 1C is a partial enlarged view of the hip prosthesis of FIG. 1 showing steps with an alternate construction to those of FIG. 1A on the periphery of the prosthesis;

FIG. 1D is a cross-sectional view of FIG. 1 along the line D—D in the direction of the arrows illustrating one of many possible cross-sections;

DETAILED DESCRIPTION OF THE INVENTION

Figure 2:
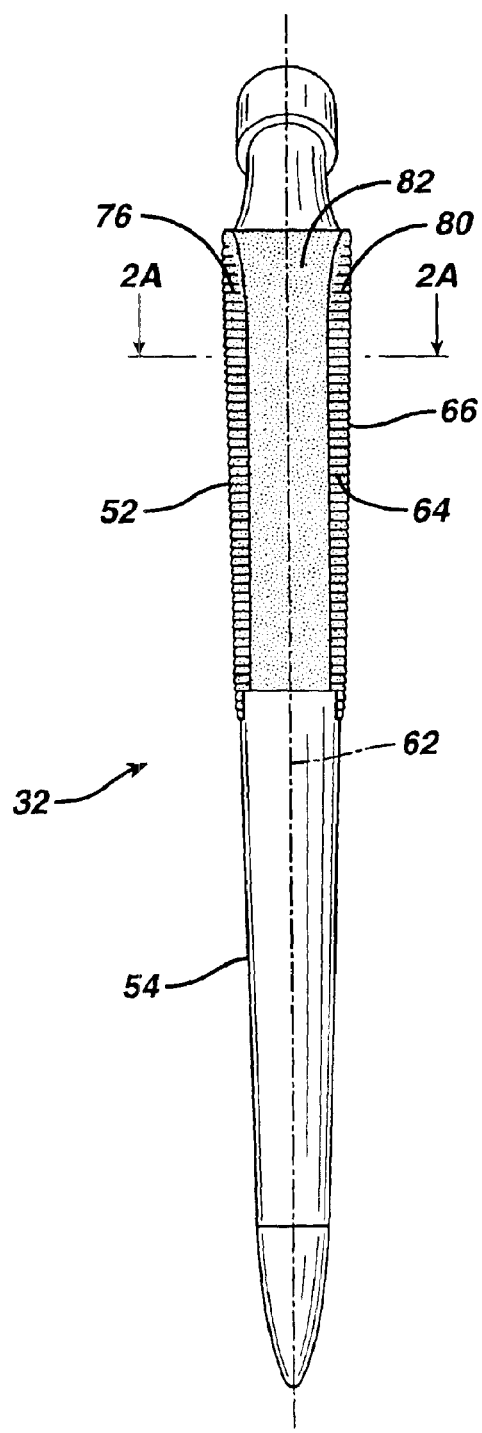
FIG. 2 is a lateral end view of a hip prosthesis in accordance with the embodiment of the present invention of FIG. 1.

Embodiments of the present invention and the advantages thereof are best understood by referring to the following descriptions and drawings, wherein like numerals are used for like and corresponding parts of the drawings.

According to the present invention and referring now to FIG. 1, joint prosthesis 10 is shown for use in arthroplasty. Arthroplasty is a well known procedure for the treatment of osteoarthritis. For a further explanation of arthroplasty may be found in Charnley, Sir John. *Low Friction Arthroplasty of the Hip*. New York: Springer, Verlock, Berlin, and Heidelberg, 1979 incorporated herein by reference in its entirety.

The joint prosthesis 10 is positioned in a long bone 12. While the long bone 12 may be any long bone within the human anatomy, the present invention is particularly well suited for long bones which have a arcuate shape particularly adjacent the resected portion of the bone. For example, the long bone 12 may be in the form of a humerus or, as shown in FIG. 1, a femur.

The femur 12 is resected along resection line 14 relieving the epiphysis 16 from the femur 12. The epiphysis is shown as dashed line 11.

The prosthesis 10 is implanted in the femur 12 by positioning the prosthesis 10 in a cavity 20 formed by reaming a portion of cancellous bone 22 within medullary canal 24 of the femur 12.

The cavity 20 may be formed in the cancellous bone 22 of the medullary canal 24 by either broaching or reaming or other similar techniques to remove the cancellous bone 22 from the canal 24. As shown in FIG. 1, the cavity 20 extends from metaphysis 26 into diaphysis 30 of the femur 12.

Any suitable combination of drilling, reaming or broaching can be used to form a cavity which corresponds closely to the periphery of the prosthesis. Typically, a broach (not shown) is driven into the medullary canal to form the cavity. This broach has a shape generally only slightly smaller than the portion of the implant that fits into the canal 24 so that the prosthesis is press fitted into the cavity 20.

Preferably and as shown in FIG. 1, the prosthesis 10 includes a body or stem 32, a portion of which is positioned within the cavity 20 of the femur 12, and a cup 34 which is connected to natural acetabulum 36. The stem 32 is pivotally connected to the cup 34. The stem 32 may be in direct contact with the cup 34 or may, as shown in FIG. 1, include a liner or bearing 40 positioned between the cup 34 and the stem 32.

The cup 34 may be made of any suitable, durable material which is compatible with the human anatomy. For strength and durability typically the cup 34 is made of a metal such as stainless steel, a cobalt chrome alloy or titanium or may be made of a ceramic.

The liner 40 may be made of any suitable, durable bearing material and is often made of polyethylene for example ultrahigh molecular weight polyethylene.

While the stem 32 may be made of unitary construction typically the stem 32 includes a stem portion 42 and a head portion 44. The two-part construction of the stem 32 provides for easier manufacture and for providing varying offsets for the prosthesis by utilizing a plurality of head portions 44 and/or a plurality of stem portions 42.

The stem portion 42 may be connected to the head portion 44 in any suitable fashion. For example, the stem portion 42 may include a male taper portion 46 which mates with a female taper portion 50 on the head portion 44.

As shown in FIG. 1, the stem portion 42 includes a proximal stem portion 52, a distal stem portion 54 extending downwardly from the proximal stem portion, and a neck portion 56 extending upwardly from the proximal stem portion 52. The proximal stem portion 52 and the distal stem portion 54 are located within the cavity 20 formed within the cancellous bone 22 of the medullary canal 24.

Hip prosthesis are secured to the medullary canal of the femur typically either by a press-fit with the medullary canal or with the use of a cement mantel which is positioned between the prosthesis and the cancellous bone. In utilizing a cement mantel the cavity is broached or reamed slightly larger than the stem and a quantity of cement (for example, PMMA—polymethylmethacrylate) is placed within the cavity and the stem inserted therein. A small uniform layer of, for example, 1–4 mm of cement is formed between the stem portion 42 and the femur 12. While the present invention may have some value for use in prosthesis having stems which utilize a cement mantel, the present invention is generally directed toward a prosthesis having a stem which is press-fitted into the cancellous bone.

As body load or weight is transferred through the torso from the acetabulum 36 to the femur 12 the load is transmitted along trabeculae or load lines 60. These trabeculae or load lines 60 are positioned in a direction generally conforming to the length of the femur and are curved in a direction toward the head of the femur.

In the diaphysis 30 or the more distal portion of the femur 12, the load lines 60 are generally linear and run parallel to longitudinal axis 62 of the femur 12. This is mainly due to the fact that the femur 12 within the diaphysis has a generally circular cross-section in a generally cylindrical shape.

On the other hand, within the metaphysis 26 the trabeculae or load lines 60 have a curved or arcuate shape or path and digress continually from the longitudinal axis 62 in the proximal direction.

According to Wolff's Law, hypertrophy is defined as a thickening of the cortex with retention of normal cortical texture. According to Wolff's Law, the hypertrophy will occur at the area of highest stress surrounding an implant. The thickening of the cortex caused by the hypertrophy is a very desirable event in the postoperative patient. For many implants within a femur the location of hypertrophy is often at the distal end of the implant. This is caused by the artificially raised stress at the point of sudden transition from the flexible distal femur to the artificially stiffened proximal femur. This is true for both press-fit and cemented stems. This phenomenon of hypertrophy thus results in excellent adhesion in the diaphysis but results in a less than desirable condition between the implant and the femur in the metaphysis.

To provide for the increased loading of the femur within the metaphysis and the resulted improvements caused by hypertrophy and Wolff's Law, according to the present invention surface features 64 are located on outer periphery 66 of the proximal stem 52. The surface features 64 serve to increase the stress or load between the implant and the femur in the metaphysis 26 to thereby gain the benefit of Wolff's Law and hypertrophy within that portion of the femur.

Preferably, as shown in FIG. 1, the stem 32 has a shape generally conforming to the shape of the femur 12. Thus, typically, within the diaphysis 30, the distal stem 54 is generally circular, having a shape generally similar to the circular shape of the femur within the diaphysis 30. Similarly, within the metaphysis 26, the proximal stem 52 has a generally oval cross-section and an arcuate orientation in the direction toward the acetabulum 32.

Further the proximal stem 52 becomes larger in the direction of the acetabulum 36. This curving, oval and enlarging toward the acetabulum configuration of the proximal stem provides a shape generally conforming to the cancellous bone within the metaphysis 26 of the femur 12.

Figure 4:
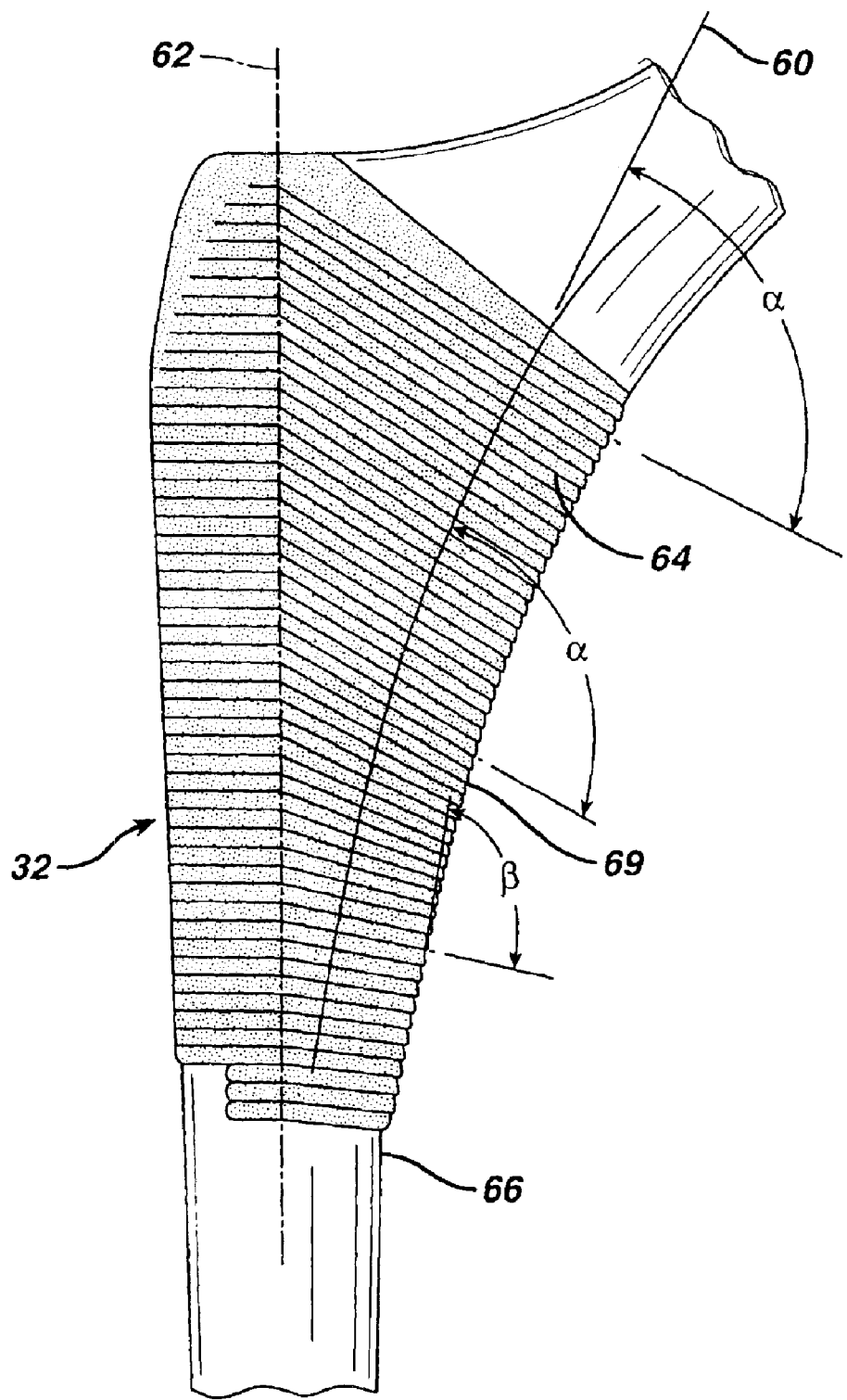
FIG. 4 is a partial plan view of the hip prosthesis of FIG. 1.
Figure 5:
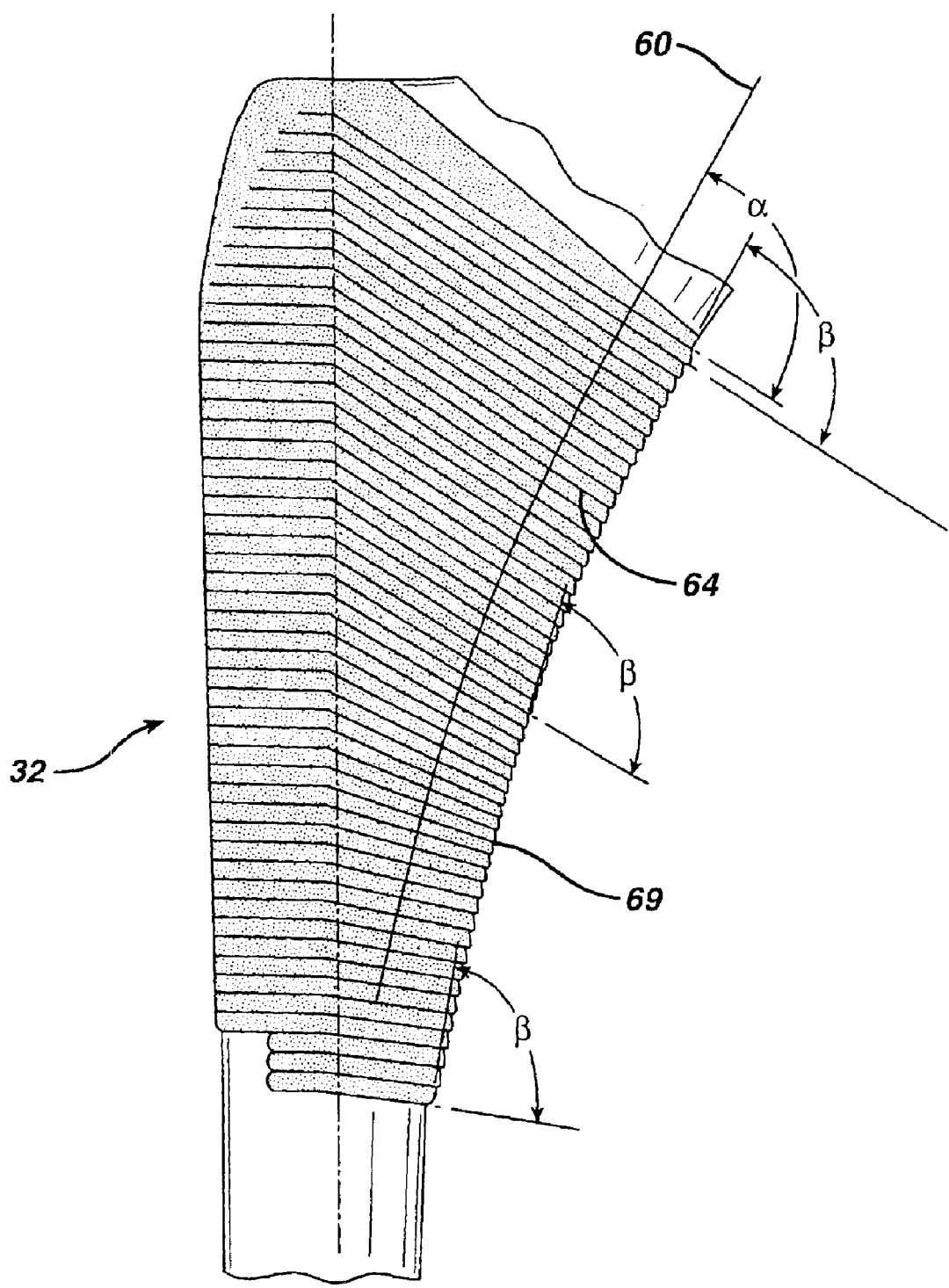
FIG. 5 is a partial plan view of the hip prosthesis of FIG. 4.

According to the present invention and referring now to FIGS. 1, 4 and 5, the applicants have found that the surface features 64 should be positioned in an orientation to optimally transfer load between the stem 32 and the femur 12.

Applicants have further found that the surface features 64 should be positioned in an orientation relative to the load lines or trabeculae 60. The load lines or trabeculae 60 pass through the proximal cancellous bone 22. The load lines 60 also pass through cortical bone or cortex 65. The cortical bone 65 has layers or normal lamellae 71 through which the load lines pass and which are concurrent therewith.

The orientation of the surface features 64 to the load lines 60 is defined by angle α. Applicants have further found that the surface features 64 should be optimally positioned in an orientation generally normal to the load lines or trabeculae 60 or that the angle α is optimally around about 90 degrees.

While the benefit of positioning the steps in relationship to the load lines or trabeculae are optimized when the steps are positioned generally normally or perpendicular to the load lines. It should be appreciated that the invention may be practiced where the steps 64 are positioned less than an ideal 90 degrees or normal to the load lines. For example, the steps may be positioned from about 70 degrees to about 110 degrees with respect to the trabeculae or load lines.

While the steps are optimally positioned generally normally or perpendicular to the load lines 60, it should be appreciated that every long bone in every person's anatomy has a different anatomical shape. For example, referring to FIG. 1, the long bone may have a shape other than that of long bone 12. The long bone may have a shape as shown in long bone 13 or as shown in long bone 15, both shown as dashed lines.

While it might be ideal to make an individual, customized prosthesis with surface features designed and manufactured optimally normal to the load lines, this is probably not economically feasible. Applicants have thus found that the invention may, thus, be commercially practiced by designing the surface features 64 to be selected to be optimally positioned generally normal to the load lines or to have at the surface features designed to be aligned around 70 to 110 degrees from the load limes for a average or normal femur or long bone. The outer periphery 66 of the proximal stem 52 is typically designed to be positioned within and to be spaced from and to conform generally to the inner periphery 67 of the cortical bone 65 of an average femur or long bone. The outer periphery 66 thus, preferably, generally conforms to inner periphery 67 of the cortical bone 65 of the long bone to which it was designed.

Referring again to FIG. 1, since the load lines 60 pass through normal lamellae of the cortex 65 and are concurrent therewith, the inner periphery 67 of the cortex 65 is generally in alignment with the load lines 60. As stated earlier, to optimized the positioning of the surface features 64, the features 64 are positioned normal to the load lines and the inner periphery 67 of the cortex 65.

Thus, for an average long bone to which a prosthesis 10 is designed, the outer periphery 66 of the proximal stem 52 conforms generally to the load lines 60. Applicants have thus found that in commercially utilizing this invention, the prostheses may be designed and manufactured with the surface features positioned with respect to the outer periphery 66 of the proximal stem 52 of the prosthesis 10. Since the load exerted on the prosthesis is large around the proximal stem 52 at the center of the inner periphery of the medial portion of the proximal stem also known as medial periphery 69 of the outer periphery 66, the Applicants have discovered that the surface features 64 may be positioned with respect to the medial periphery 69 of the outer periphery 66

The surface features 64 form an angle β with medial periphery 69. For example, the surface features may be positioned from about 70 degrees to about 110 degrees with respect to the medial periphery 69 of the proximal stem 52 of the prosthesis 10. The surface features 64 may optimally be positioned in an orientation generally normal to the medial periphery 69 or the angle β may optimally be around about 90 degrees.

Thus, as shown in FIG. 1, in the portion of the metaphysis 26 next to the diaphysis 30, the surface features 64 run generally perpendicular to the load line 60 and also nearly perpendicular to the longitudinal axis 62. Conversely in the portion of the metaphysis 26 further from the diaphysis 30, the surface features 64 run generally perpendicular to the load line 60, but far from being perpendicular to the longitudinal axis 62.

The surface features 64 are generally in the form of grooves, ribs or ridges extending inwardly or outwardly from the surface 66. The surface feature 64 generally has a uniform cross-section as shown FIGS. 1A through 1C.

Applicants have found that by positioning the surface feature 64 in an orientation generally perpendicular to the load line 60 the supporting ability of the surface features 64 may be optimized. By optimizing the load capacity of the surface feature 64, the stress imparted from the stem 32 to the femur 12 may maximize the stress at that position. Further, because Wolff's Law encourages hypertrophy or the thickening of the cortex in the metaphysis 26 of the femur 12, the adherence and bone growth around the implant within the metaphysis area 26 is thereby improved.

The applicants have found that a large portion of the load transferred by the stem is concentrated in that portion of the stem adjacent the more curved portion of the femur 12.

Figure 2A:
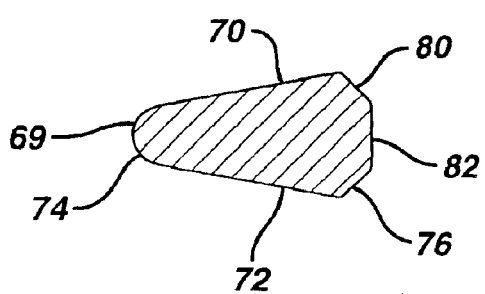
FIG. 2A is a cross-sectional view of FIG. 2 along the line A—A in the direction of the arrows illustrating one of many possible cross-sections.

For example, referring now to FIG. 2A, a typical cross section of the proximal stem 52 of the prosthesis 10 is shown. It should be appreciated that the proximal stem 32 may have any suitable cross section. Since the cross section of the proximal portion of the long bone 12 is typically oval or non-circular, a non-circular prosthesis cross section is preferred. The shape of FIG. 2A is pentagonal or five sided with a large semicircular portion on the medial side.

The surfaces 70, 72 and 74 which approximate the curved portion of the femur 12 transfer a major portion of the load between the femur 12 within the metaphysis 26. Applicants have found that if the surface features 64 are positioned generally normal or perpendicular to the load lines 60 on surfaces 70, 72 and 74 a large majority of the benefit of providing the surface features generally normal to the load lines may be accomplished. Thus the surface features 64 located on other surfaces, for example, surfaces 76, 80 and 82 may be oriented in directions other than normal to the load lines or surface features 64 may be omitted from the surfaces 76, 80 and 82.

Referring now to FIG. 1A, to optimize the load carrying or stress increasing capacity of the surface features 64, the surface features as shown in FIG. 1A may be in the form of steps or terraces. Such steps or terraces are more fully shown in U.S. Pat. No. 4,790,852 to Noiles and incorporated herein by reference in its entirety. The terraces 64 have an inner edge 84 and an outer edge 86. A ledge 90 is formed between outer edge 86 and inner edge 84. The ledge is positioned distally and serves to provide optimum support or stress for the stem 32. The terraces 64 has a vertical spacing -V- between terraces of approximately 0.50 to 3.0 mm and a depth -D- of approximately 0.2 mm to 1.5 mm.

It should be appreciated that while the terraces 64 as shown in FIG. 1A are preferred, the invention may be practiced with other types of surface features. For example, as shown in FIG. 1B, the surface features may be in the form of ribs 164 which provide an angled support surface 190.

Alternatively referring to FIG. 1C, the surface features may be in the form of grooves 164' which extend inwardly from the surface.

To further promote bone growth between the stem and the femur and referring again to FIG. 1A, the surface 66 of the surface features 64 may be coated by a coating 92. The coating 92 may be any coating which promotes bone growth and/or interconnections between the prosthesis and the femur. For example the coating 92 may be a bio-ceramic. Such suitable bio-ceramics include hydroxyapatite or tricalcium phosphates. Alternatively, the coating 92 may be a porous coating. Alternatively, the coating may be a porous coating and a bio-ceramic coating in combination.

Various porous coatings have found to be very effective. One particularly effective coating is sold by the Assignee of the instant application under the tradename Porocoat. The Porocoat coating is more fully described in U.S. Pat. No. 3,855,638 to Pilliar and hereby incorporated herein by reference in its entirety.

This porous coating consists of a plurality of small discreet particles of metallic material bonded together at their points of contact with each other to define a plurality of connected interstitial pores in the coating. The particles are of the same metallic material as the metallic material from which the substrate is formed. Examples of suitable material include austenitic stainless steel, titanium, titanium alloys and cobalt alloys.

The stem 32 may be made of any suitable durable material and, for example, may be made of a titanium, a cobalt chrome molybdenum alloy or stainless steel. The applicants have found that titanium TI-6AL-4V is well suited for this application.

It should be appreciated that while, as shown in FIG. 1, the proximal stem 52 has a taper design, the aligning of surface features with respect to the load lines of the present invention may be practiced with the taper design or with a non-taper design. Further it should be appreciated that while, as shown in FIG. 1, the prosthesis 10 is shown with a coating 92, the invention may be practiced without the porous coating 92.

The terraces 64 are aligned in a direction generally normal to the medial curve or load line 64 on the anterior face 70, the medial arcuate surface 74 and the posterior surface 72. The terraces 64 become horizontal as they approach the lateral aspect of the implant, (surfaces 76, 80 and 82) (see FIG. 2A) to align roughly normal to the lateral face of the implant.

Referring now to FIG. 2, the stem 32 is shown in an anterior/posterior view. The stem 32 is shown with the distal stem 54 not including the surface features or terraces 64. The proximal stem 52 however includes the terraces 64 on posterior lateral surface 76 and on anterior lateral surface 80. As shown in FIG. 2, the proximal stem 52 does not have terraces 64 in the lateral surface 82.

As shown in FIG. 2 the terraces 64 on the posterior lateral surface 76 and the anterior lateral surface 80 are generally perpendicular to longitudinal axis 62. It should be appreciated that the terraces 64 on surfaces 76 and 80 may be positioned normal to the load lines 60. However, since most of the benefit of the positioning of the surface features 64 normal to the load line 60 is accomplished on surfaces 70 and 72, for simplicity of design and manufacture, the terraces 64, as shown in FIG. 2, may be positioned normal to the longitudinal axis 62. Further, for simplicity and ease of manufacture, the lateral surface 82, as shown in FIG. 2, may be made without terraces 64.

Figure 3:
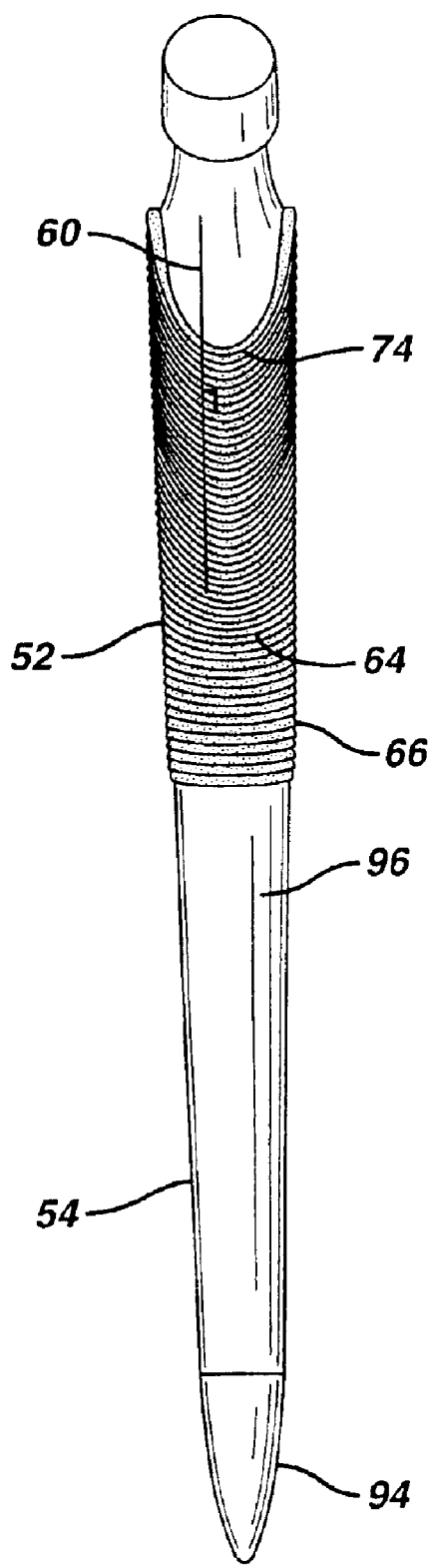
FIG. 3 is a medial end view of a hip prosthesis in accordance with the embodiment of the present invention of FIG. 1.

Referring now to FIG. 3 the stem 32 is shown in a posterior/anterior position. The medial surface 74 is shown with terraces 64 on surface 66 in the proximal stem 52. The terraces 64 are positioned normal to load lines 60.

As shown in FIG. 3 the distal stem 54 may include a polished tip 94 extending a distance of, for example, one-half to one inch from the distal end of the stem 32. The distal stem 54 may, for example, be grit blasted in the remaining portion 96 of the distal stem 54.

Figure 6:
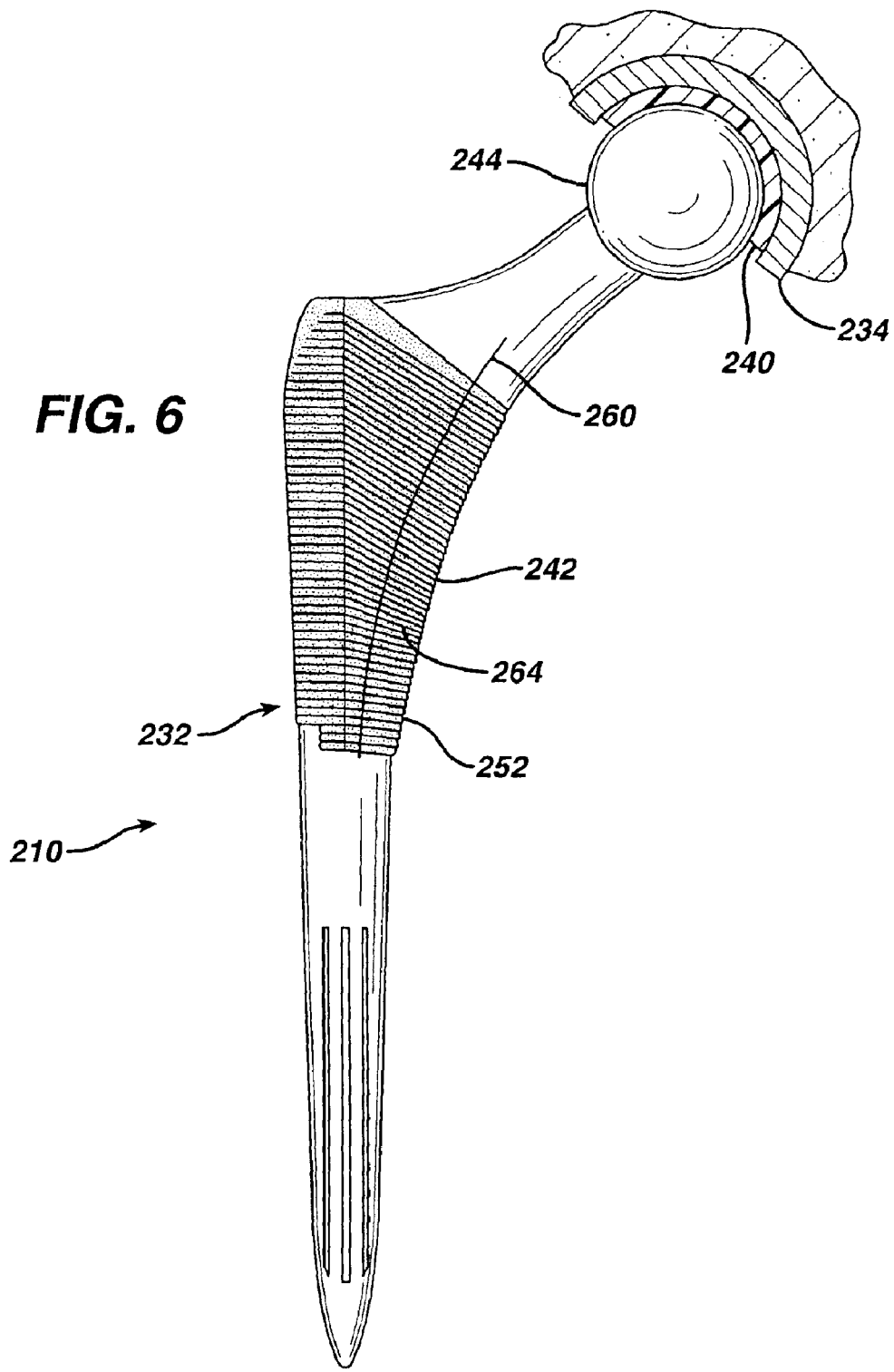
FIG. 6 is a plan view of a hip prosthesis in accordance with another embodiment of the present invention.

Referring now to FIG. 6, an alternate embodiment of the present invention is shown as prosthesis 210. Prosthesis 210 is similar to prosthesis 10 of FIG. 1 except that, whereas prosthesis 10 of FIG. 1 includes a separate stem and head which are connectable together, the prosthesis 210 includes a head portion 244 which is integral with stem portion 242. Prosthesis 210 includes stem 232 which is pivotally connected to cup 234 and includes a bearing or liner 240 placed therebetween.

As with prosthesis 10, prosthesis 210 includes steps 264 similar to steps 64 of prosthesis 10 which steps 264 are positioned generally normal or perpendicular to load lines or trabeculae 260. As in the prosthesis 210 the steps 264 are positioned on the proximal stem 252 of the stem 232. The steps 264 are preferably similar to the steps 64 of the prosthesis 10 of FIG. 1.

Figure 7:
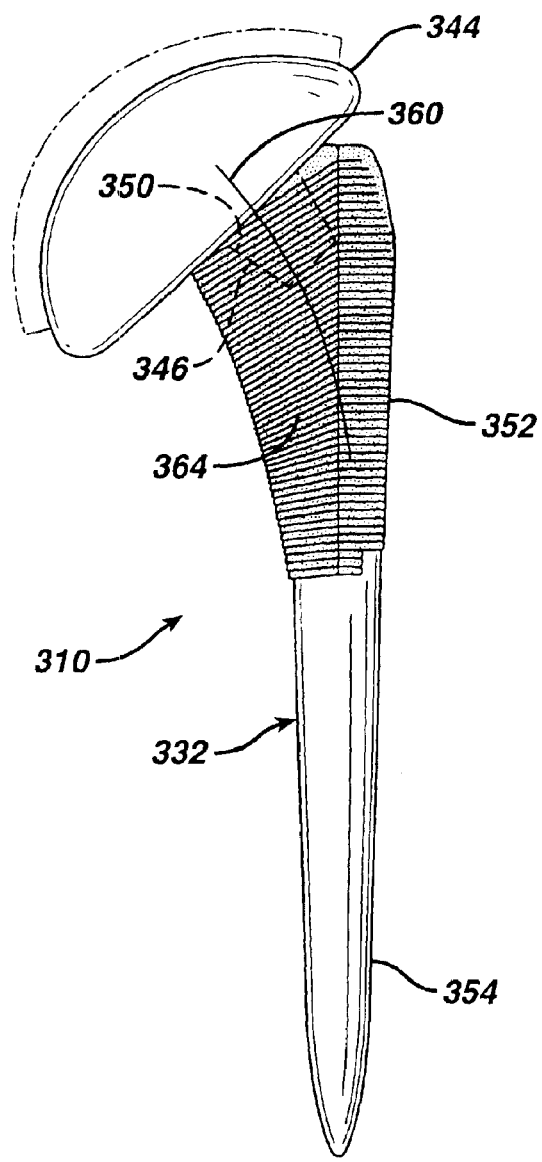
FIG. 7 is a plan view of a shoulder prosthesis in accordance with a further embodiment of the present invention.

Referring now to FIG. 7 an alternate embodiment of the present invention is shown as shoulder prosthesis 310. The shoulder prosthesis 310 includes a stem 332 which is implanted into a humerus (not shown). The prosthesis 310 also includes a head portion 344 attached to the stem 322. The head portion 344 may be secured to the stem 322 in any suitable manor and may alternatively be integral therewith. The head portion may have a external taper 346 extending therefrom which mates with an internal taper 350 in the stem 332.

Such a configuration is shown in U.S. Pat. No. 5,314,479 to Rockwood et al. incorporated by reference herein in its entirety. The stem portion 342 of the stem 332 includes a proximal stem 352 and a distal stem 354. For the same reasons expressed with regard to the prosthesis 10 of FIG. 1, the prosthesis 310 includes steps 364 similar to the steps 64 of the FIG. 1 prosthesis. The steps 364 are aligned generally perpendicular or normal to the trabeculae or load lines 360. For the same reasons expressed with regard to the FIG. 1 prosthesis 10, the steps 364 are preferably positioned on the proximal stem 352.

Figure 7A:
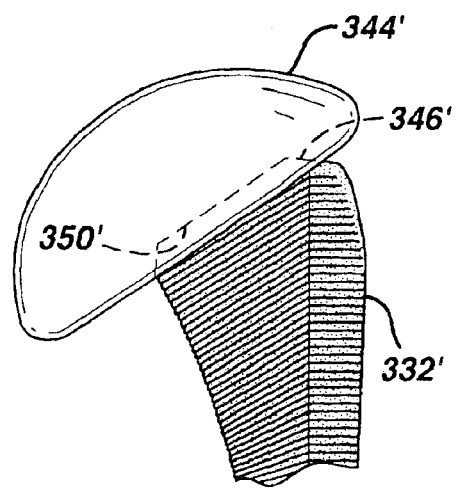
FIG. 7A is a partial plan view of the shoulder prosthesis of FIG. 7 showing an alternate stem-shoulder connection.

Referring now to FIG. 7A, a alternate securing arrangement is shown for connecting the head portion to the stem. In this arrangement the stem 332' may have a external taper 346' extending therefrom which mates with an internal taper 350' in the head portion 344'. Such a configuration is shown in U.S. Pat. No. 6,120,542 to Camino et al. incorporated by reference herein in its entirety.

Figure 8:
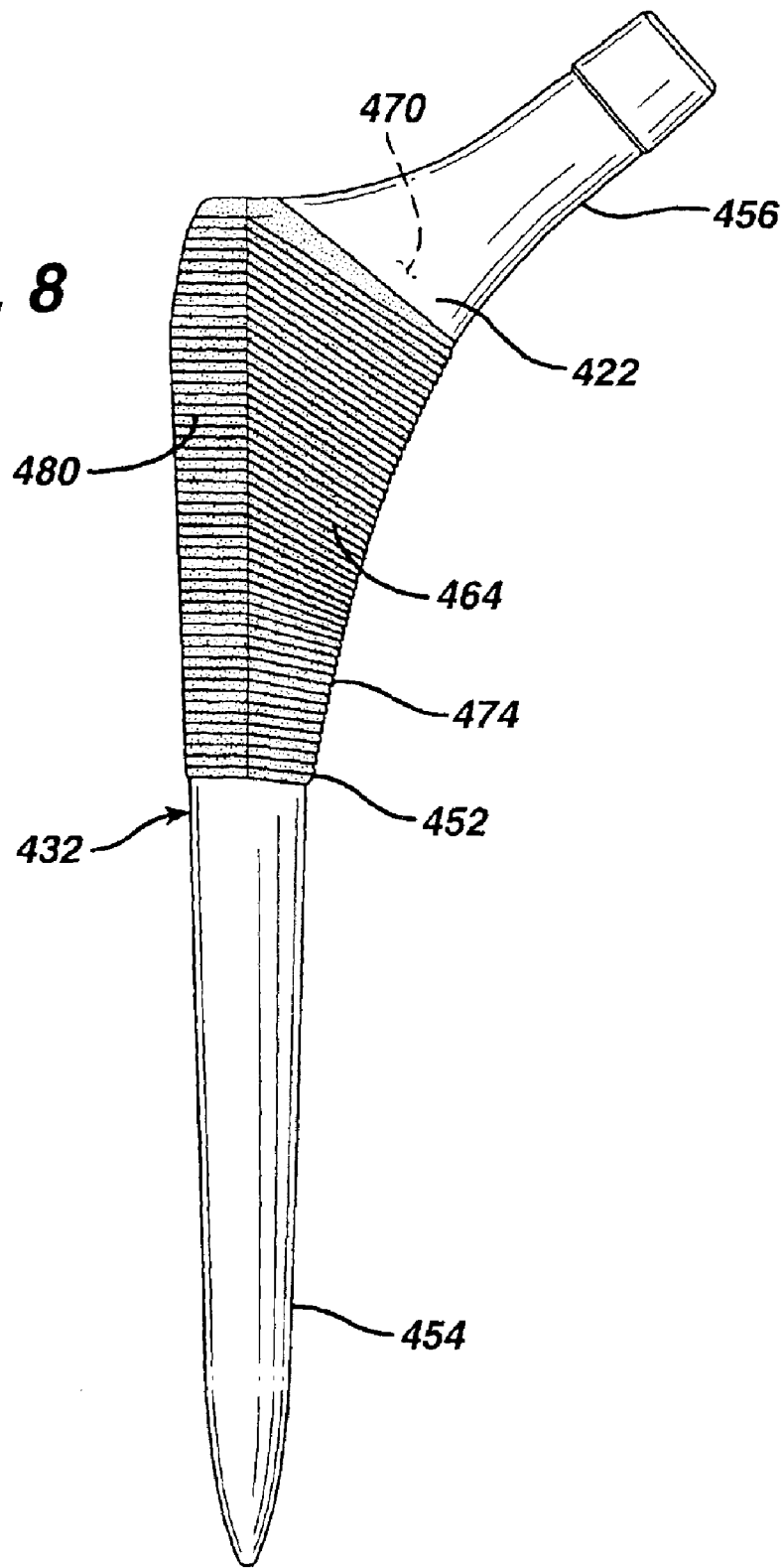
FIG. 8 is a plan view of a hip prosthesis in accordance with a further embodiment of the present invention.
Figure 9:
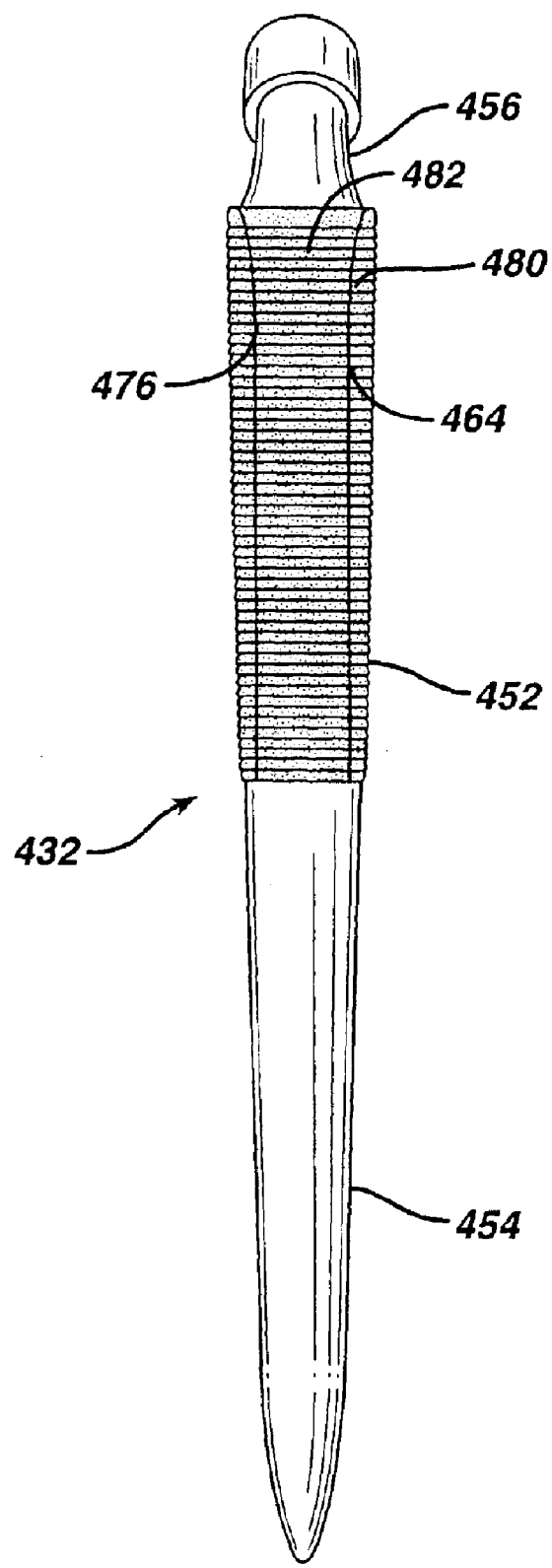
FIG. 9 is a lateral end view of a hip prosthesis in accordance with the embodiment of the present invention of FIG. 8.
Figure 10:
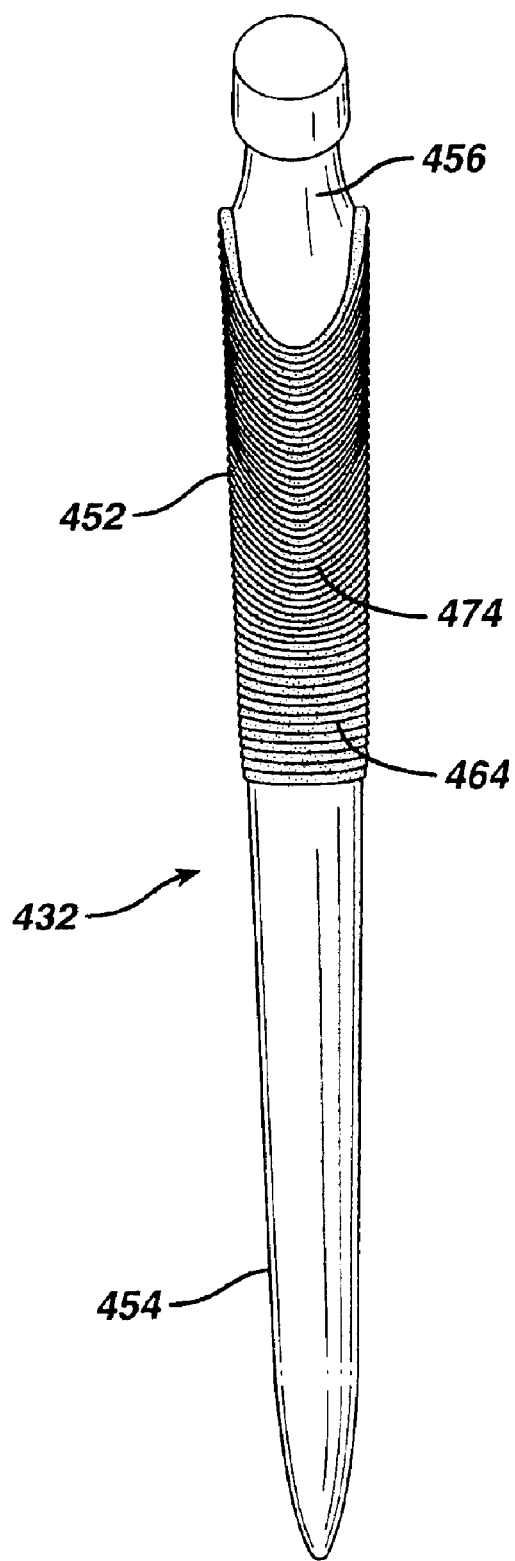
FIG. 10 is a medial end view of a hip prosthesis in accordance with the embodiment of the present invention of FIG. 8.

Another embodiment of the present invention is shown in FIGS. 8 through 10 as stem portion 432. Stem portion 432 is similar to stem portion 32 of the FIG. 1 prosthesis except that the proximal stem 452 of the stem portion 432 includes steps 464 similar to the step 64 of the prosthesis 10 which steps 464 are positioned completely around the periphery of the proximal stem 452.

Referring now to FIG. 8, the stem portion 432 includes the distal stem 454, the proximal stem 452 and neck portion 456. The steps 464 are positioned completely around the periphery of the proximal stem 452. In fact the steps 464 are positioned on the anterior face 472, the anterior lateral face 480 and the posterior face 470.

Referring now to FIG. 9 the steps 464 are positioned on the posterior lateral face 476, on the lateral face 482 and on the anterior lateral face 480.

Referring now to FIG. 10 the steps 464 are also positioned on the medial face 474 of the proximal stem 452.

Figure 11:
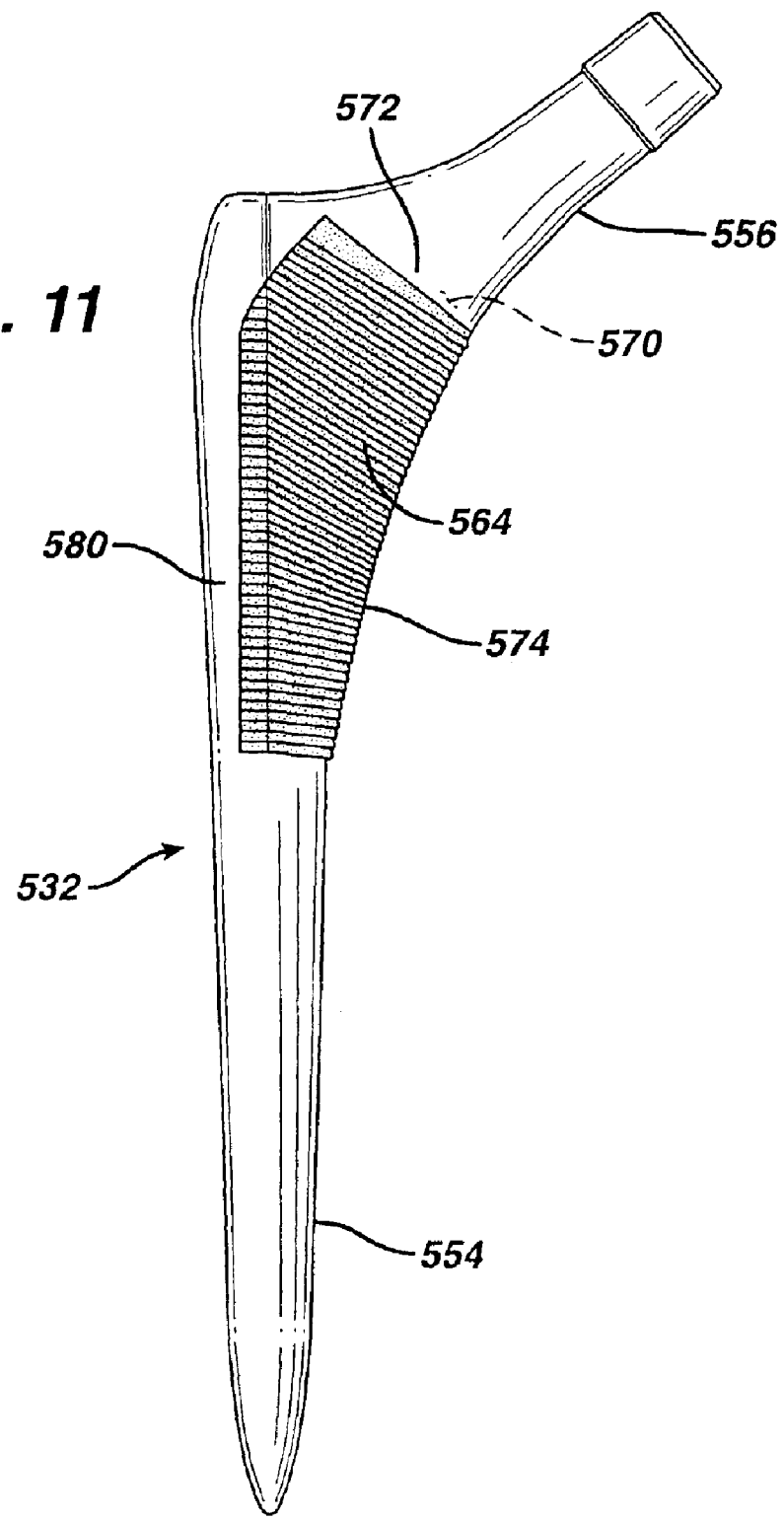
FIG. 11 is a plan view of a hip prosthesis in accordance with another embodiment of the present invention.
Figure 12:
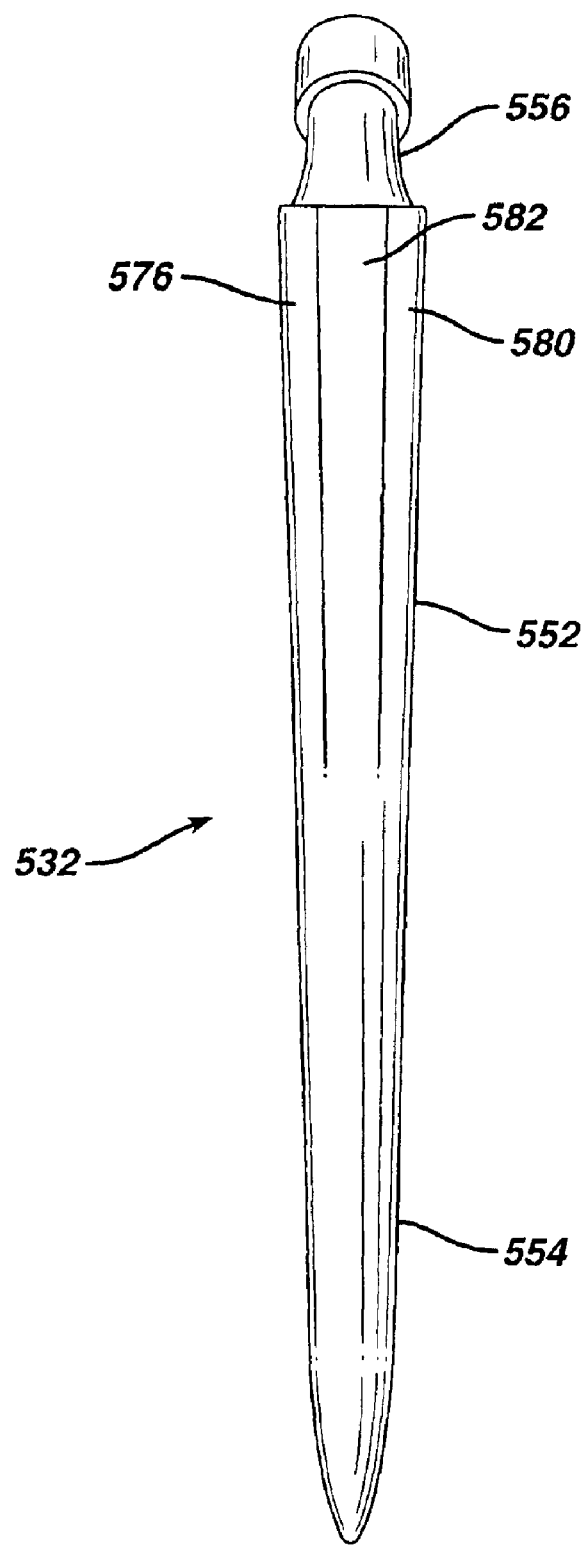
FIG. 12 is a lateral end view of a hip prosthesis in accordance with the embodiment of the present invention of FIG. 11.
Figure 13:
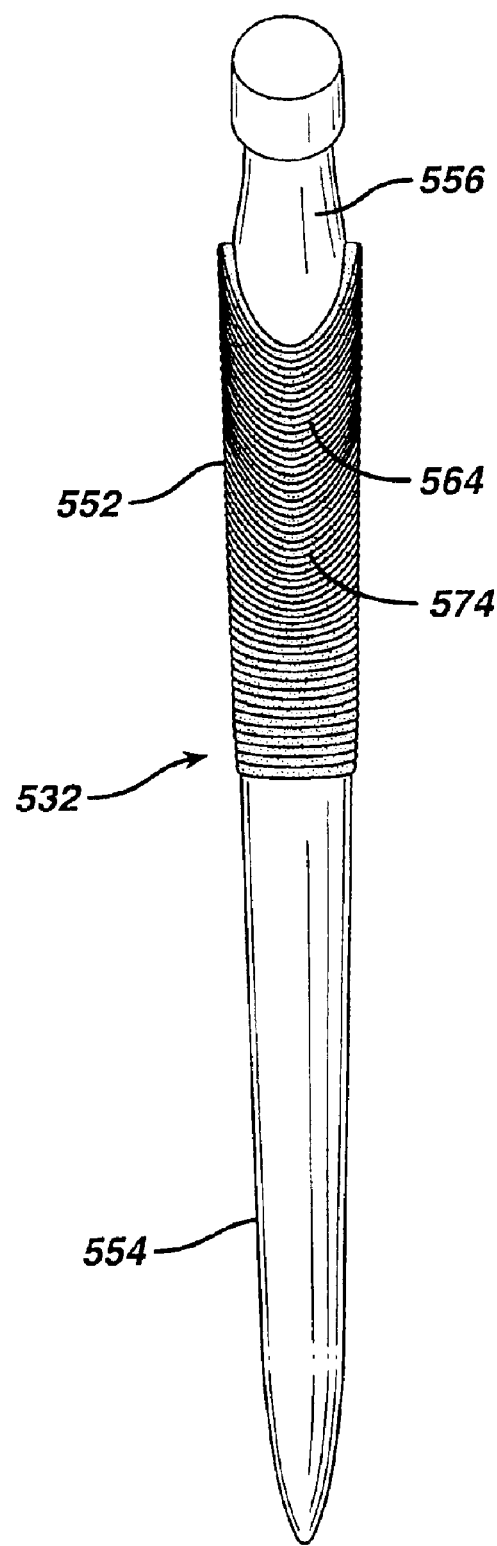
FIG. 13 is a medial end view of a hip prosthesis in accordance with the embodiment of the present invention of FIG. 11.

Referring now to FIGS. 11, 12 and 13 a further embodiment of the present invention is shown as a stem portion 532. Stem portion 532 is similar to stem portion 32 of the FIG. 1 prosthesis except that steps 564, which are similar to steps 64 of the FIG. 1 prosthesis, are positioned only on the anterior, posterior and medial faces.

Referring now to FIG. 11, the stem portion 532 includes a distal stem 554, a proximal stem 552 and a neck portion 556. The steps 562, similar to the steps 64 of the FIG. 1 prosthesis 10, are positioned only on the proximal stem of 552. The Applicants have found since the loading on the stem portion 532 is primarily on the anterior, posterior and medial faces, the invention may be practiced with steps 562 positioned only on these faces. In fact, the invention may be practiced with the steps on perhaps less than these three faces.

As shown in FIG. 11 the steps 562 are located on the medial face 574, the posterior face 570 and the anterior face 572. The anterior lateral face 580, as shown in FIG. 11, does not include the steps 564.

Referring now to FIG. 12, no steps 562 are positioned on the posterior lateral face 576, on the lateral face 582 and on the anterior lateral face 580.

Referring now to FIG. 13 the medial face 574 of the proximal stem of 552 includes these steps 564.

By providing a prosthesis which has a stem with steps which are aligned in a direction generally normal to the load lines or trabeculae of the prosthesis load carrying capacity of the proximal femur may be optimized. By optimizing the loading of the proximal femur, a manifestation of Wolff's Law can occur which causes the raised stresses at the greatest loading to create a thickening of the cortex and improvement of the bone growth and adherence of the prosthesis to the proximal femur.

By providing a prosthesis having surface features in the form of steps which are positioned generally normal to the load lines of the prosthesis, the prosthesis may benefit from a long term stability and fixation by providing an environment optimum for femoral bone remodeling.

Although the present invention and its advantages have been described in detail, it should be understood that various changes, substitutions, and alterations can be made therein without departing from the spirit and scope of the present invention as defined by the appended claims.

What is claimed:

1. A ball and socket joint joint prosthesis for use in arthroplasty comprising:

a body for implantation at least partially within the medullary canal of a long bone defining trabeculae in the proximal cancellous bone thereof and defining lamellae in the cortical bone thereof, said body including a proximal portion thereof and a distal portion thereof, said proximal portion having a medial periphery thereof, said proximal portion including surface features thereof on a substantial portion of said proximal portion, said surface features being positioned to optimally transfer load from the prosthesis to the long bone, wherein said surface features are elongated in a first direction of said features; and wherein said surface features are positioned so that the first direction of said features are from about 70 degrees to about 110 degrees with respect to the proximal portion of said body, wherein said surface features are elongated in a first direction of said features, and wherein said surface features are positioned so that the first direction of said features are substantially normal to the medial periphery of the proximal portion of said body.

2. A joint prosthesis for use in arthroplasty comprising:

a body for implantation at least partially within the medullary canal of a long bone defining trabeculae in the proximal cancellous bone thereof and defining lamellae in the cortical bone thereof, said body including a proximal portion thereof and a distal portion thereof, said proximal portion having a medial periphery thereof, said proximal portion including surface features thereof on a substantial portion of the medial periphery of said proximal portion, said surface features being positioned to optimally transfer load from the prosthesis to the long bone wherein said surface features are elongated in a first direction of said features.

3. The joint prosthesis of claim 2:

wherein said surface features comprise a plurality of ribs elongated in a first direction of said features.

4. The joint prosthesis of claim 3, wherein at least a portion of the surface of said ribs is adapted to enhance bone growth thereto.

5. The joint prosthesis of claim 4, wherein at least a portion of the surface of said ribs comprises at least one of a surface roughness, a porous coating and a bioceramic.

* * * * *